United States Patent
Jeon et al.

(10) Patent No.: US 7,248,911 B2
(45) Date of Patent: Jul. 24, 2007

(54) METHOD AND APPARATUS FOR NONINVASIVELY MEASURING A CONCENTRATION OF A BLOOD COMPONENT

(75) Inventors: Kye-jin Jeon, Suwon-si (KR); Gil-won Yoon, Seoul (KR); In-duk Hwang, Suwon-si (KR); Sang-joon Han, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 399 days.

(21) Appl. No.: 10/802,920

(22) Filed: Mar. 18, 2004

(65) Prior Publication Data

US 2004/0186364 A1    Sep. 23, 2004

(30) Foreign Application Priority Data

Mar. 19, 2003    (KR) .......................... 10-2003-17137

(51) Int. Cl.
    *A61B 5/00*    (2006.01)
(52) U.S. Cl. ...................................... 600/335; 600/322
(58) Field of Classification Search ................ 600/310, 600/322, 334, 335, 345
    See application file for complete search history.

(56) References Cited

U.S. PATENT DOCUMENTS

| | | | |
|---|---|---|---|
| 5,077,476 A | 12/1991 | Rosenthal | ................... 250/341 |
| 5,127,406 A | 7/1992 | Yamaguchi | |
| 5,183,042 A * | 2/1993 | Harjunmaa et al. | ......... 600/309 |
| 5,372,135 A | 12/1994 | Mendelson et al. | ......... 128/633 |
| 5,379,764 A | 1/1995 | Barnes et al. | ............... 128/633 |
| 5,912,730 A | 6/1999 | Dahm et al. | |
| 6,078,828 A * | 6/2000 | Yasuda et al. | ............... 600/310 |
| 6,113,541 A | 9/2000 | Dias et al. | ................... 600/301 |
| 6,213,952 B1 | 4/2001 | Finarov et al. | ............. 600/491 |
| 6,285,894 B1 * | 9/2001 | Oppelt et al. | ............... 600/322 |
| 6,400,972 B1 | 6/2002 | Fine | |
| 2003/0204133 A1 | 10/2003 | Harjunmaa et al. | |

FOREIGN PATENT DOCUMENTS

| | | |
|---|---|---|
| CN | CN 1 315 844 | 10/2001 |
| EP | 0 967 477 | 12/1999 |

* cited by examiner

*Primary Examiner*—Eric Winakur
*Assistant Examiner*—Etsub Berhanu
(74) *Attorney, Agent, or Firm*—Lee & Morse, P.C.

(57) ABSTRACT

In an apparatus and method of noninvasively measuring a concentration of a blood component, the method includes (a) varying a thickness of a body part of a subject, measuring absorption spectrums at different thicknesses of the body part, obtaining a first differential absorption spectrum between the absorption spectrums measured at different thicknesses, actually measuring concentrations of the blood component, and establishing a statistical model using the first differential absorption spectrum and the actually measured concentrations; and (b) estimating the concentration of the blood component using a second differential absorption spectrum obtained with respect to the body part based on the statistical model.

21 Claims, 14 Drawing Sheets

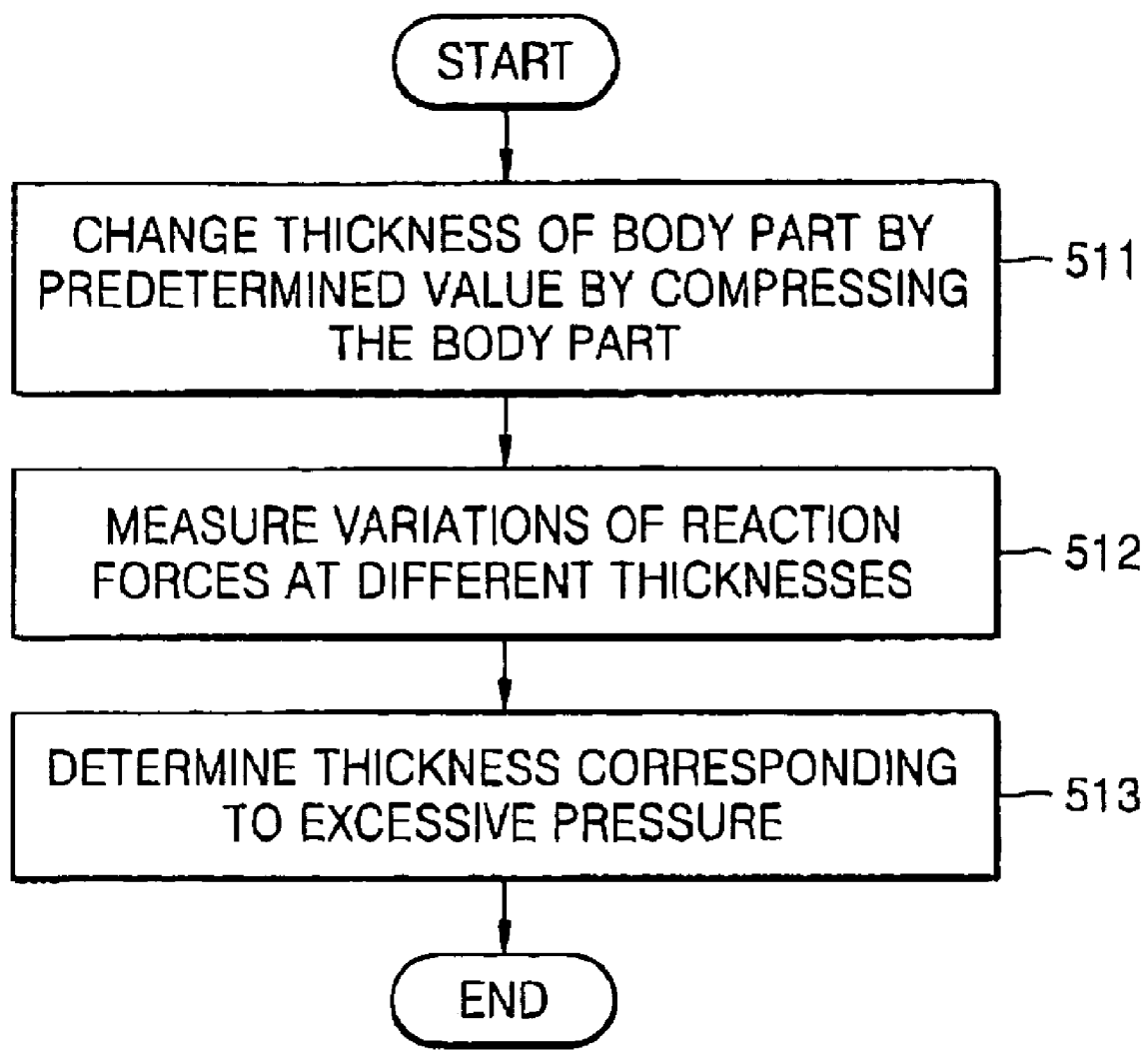

METHOD AND APPARATUS FOR NONINVASIVELY MEASURING A CONCENTRATION OF A BLOOD COMPONENT

BACKGROUND OF THE INVENTION

1. Field of the Invention

The present invention relates to a noninvasive measurement of a concentration of a blood component. More particularly, the present invention relates to a method and apparatus for noninvasively measuring a concentration of a blood component using a differential absorption spectrum corresponding to a variation of amounts of blood and interstitial fluid in a blood vessel, the variation being generated by varying a thickness of a particular soft tissue of a subject.

2. Description of the Related Art

With overall improvements in quality of life and living conditions, interest in personal health has increased. As a result, a wide array of home medical equipment that allows people to easily monitor their personal health has been researched and developed. In a normal human body, bodily fluid is organically circulated and adjusted so that an amount of bodily fluid is maintained within a predetermined range. Bodily fluids include blood, urine, interstitial fluid, sweat, and saliva. In particular, concentrations of blood and urine (glucose and protein) are essential parameters in determining a person's state of health. In addition, concentrations of blood components, such as glucose, hemoglobin, bilirubin, cholesterol, albumin, creatinine, protein, and urea, play an important role in assessing a person's state of health.

When a human body is infected with a disease, a composition or amount of a component of a bodily fluid changes, which may result in death. For example, a normal person's blood glucose concentration is about 80 mg/dl before meal and about 120 mg/dl after meal. In order to maintain such a normal glucose concentration, a human pancreas secretes an appropriate amount of insulin before or after the meal so that glucose can be absorbed into the liver and skeletal muscle cells. However, when the pancreas does not secrete an appropriate amount of insulin to maintain a normal blood glucose concentration due to a disease or other causes, an excessive amount of glucose exists in the blood, which causes a disease of the heart or the liver, arteriosclerosis, hypertension, cataract, retinal bleeding, nerve damage, hearing loss, or visual disturbance, all of which may cause serious problems including death. Accordingly, a technique of measuring a change in a bodily fluid of a human body is considered very important.

Methods of measuring a concentration of a component of a bodily fluid include invasive methods of directly collecting a sample of a target matter and performing measurement on the collected sample of the target matter and noninvasive methods of performing measurement without directly collecting a target matter. Since invasive methods have many problems, techniques of easily analyzing components of a bodily fluid using a noninvasive method have been continuously researched and developed. Conventionally, when measuring a component of a bodily fluid, for example, blood glucose, blood is extracted, reacted with a reagent, and then analyzed by using a clinical analysis system or quantifying a change in color of a test strip. When such a blood glucose test is performed every day, a patient suffers pain resulting from the direct blood collection and is susceptible to infection. Moreover, since it is difficult to continuously monitor the blood glucose level, it is difficult to properly treat a patient in an emergency situation. In addition, use of disposable strips and reagents may be a financial burden on the patient. Furthermore, these disposable strips and reagents cause environmental contamination, and as such, require special treatment. Accordingly, development of a technique of measuring a blood glucose concentration without extracting blood is desired for monitoring and adjusting a blood glucose level of a diabetic or diagnosing a person's state of health. Many methods of noninvasively measuring blood glucose have been researched, but instruments using these methods have not been commercialized.

In most conventional, spectroscopic methods for measuring a concentration of a blood component in a human body, light within a visible ray and near infrared ray (NIR) wavelength range is radiated onto a part of the body. Then, light reflected from or transmitted through the body is detected. In such spectroscopic methods, a spectrum is usually measured to measure the concentration of a blood component. Here, a reference light source having a wavelength that best responds to a blood component to be measured and a bandwidth that effectively counterbalances an influence of an interference substance is required. In addition, since a concentration of a component to be measured may be very low in blood and a light diffusion effect is greater than a light absorption effect in living tissue and blood, a detected signal is very weak. Thus, a method of amplifying the signal is required. Moreover, since organic substances in the body flow continuously, a component concentration can be accurately measured only when the measurement is quickly performed. In addition, it must be noted that an average energy radiated onto a human body should not go beyond a limit that may damage the human body. In particular, in an NIR wavelength range of about 700 through 2500 nm, a glucose absorption band is widely distributed, and glucose absorption is small as compared to a large aqueous background spectrum. Resultantly, a signal to noise ratio (SNR) is small, which makes accurate measurement very difficult.

SUMMARY OF THE INVENTION

In an effort to solve at least some of the above problems, it is a feature of an embodiment of the present invention to provide a method of noninvasively measuring a concentration of a blood component using a differential absorption spectrum corresponding to a variation of amounts of blood and interstitial fluid, the variation being generated by varying a thickness of a particular soft tissue of a subject.

It is another feature of an embodiment of the present invention to provide an apparatus capable of performing the above-described method.

According to a feature of an embodiment of the present invention, there is provided a method of noninvasively measuring a concentration of a blood component including (a) varying a thickness of a body part of a subject, measuring absorption spectrums at different thicknesses of the body part, obtaining a first differential absorption spectrum between the absorption spectrums measured at different thicknesses, actually measuring concentrations of the blood component, and establishing a statistical model using the first differential absorption spectrum and the actually measured concentrations; and (b) estimating the concentration of the blood component using a second differential absorption spectrum obtained with respect to the body part based on the statistical model.

In one embodiment of the present invention, (a) may include (a1) determining an initial thickness of the body part of the subject, (a2) increasing the thickness of the body part from the initial thickness to a first thickness and measuring a first absorption spectrum with respect to the body part, (a3) increasing the thickness of the body part from the first thickness to a second thickness and measuring a second absorption spectrum with respect to the body part, (a4) generating one of K first differential absorption spectrums between the first and second absorption spectrums, (a5) obtaining the K first differential absorption spectrums by repeating operations (a2) through (a4) K times in correspondence with K concentrations of the blood component actually measured from the subject, and (a6) establishing the statistical model of the blood component by performing multivariate statistical analysis on the K first differential absorption spectrums and the K concentrations actually measured. Further, operation (b) may include (b1) increasing the thickness of the body part from the initial thickness to the first thickness and measuring a third absorption spectrum with respect to the body part, (b2) increasing the thickness of the body part from the first thickness to the second thickness and measuring a fourth absorption spectrum with respect to the body part, (b3) generating the second differential absorption spectrum between the third and fourth absorption spectrums, and (b4) estimating the concentration of the blood component using the second differential absorption spectrum generated in operation (b3) and the statistical model. Preferably, a variation between the initial thickness and the first thickness is less than about 0.2 mm and a variation between the first thickness and the second thickness ranges from about 0.1 to 0.3 mm.

In another embodiment of the present invention, (a) may include (a1) determining an initial thickness of the body part of the subject, (a2) increasing the thickness of the body part from the initial thickness to a first thickness and holding the state in standby for a predetermined period of time, (a3) increasing the thickness of the body part from the first thickness to a second thickness and measuring a first absorption spectrum with respect to the body part, (a4) increasing the thickness of the body part from the second thickness to a third thickness and measuring a second absorption spectrum with respect to the body part, (a5) generating one of K first differential absorption spectrums between the first and second absorption spectrums, (a6) obtaining the K first differential absorption spectrums by repeating operations (a2) through (a5) K times in correspondence with K concentrations of the blood component actually measured from the subject, and (a7) establishing the statistical model of the blood component by performing multivariate statistical analysis on the K first differential absorption spectrums and the K concentrations actually measured. Further, operation (b) may include (b1) increasing the thickness of the body part from the initial thickness to the first thickness and holding the state in standby for the predetermined period of time, (b2) increasing the thickness of the body part from the first thickness to the second thickness and measuring a third absorption spectrum with respect to the body part, (b3) increasing the thickness of the body part from the second thickness to the third thickness and measuring a fourth absorption spectrum with respect to the body part, (b4) generating the second differential absorption spectrum between the third and fourth absorption spectrums, and (b5) estimating the concentration of the blood component using the second differential absorption spectrum generated in operation (b4) and the statistical model. Preferably, the predetermined period of time ranges from about 30 to 180 seconds. Preferably, a variation between the first thickness and the second thickness ranges from about 0.05 to 0.2 mm and a variation between the second thickness and the third thickness ranges from about 0.1 to 0.3 mm.

According to another feature of an embodiment of the present invention, there is provided a computer readable recording medium having recorded therein a program for executing the above method.

According to yet another feature of an embodiment of the present invention, there is provided an apparatus for noninvasively measuring a concentration of a blood component including a light source that emits light, a spectroscope that separates the light emitted from the light source into components of different wavelengths, a body-machine interface unit, which is mounted on a body part of a subject, that radiates the light from the spectroscope onto the body part, collects light transmitted through the body part, varies a thickness of the body part according to a pressure applied to the body part, and secures the body part, a detection unit that detects a first through a fourth absorption spectrum from the light collected by the body-machine interface unit, and a signal processor that generates a signal for the body-machine interface unit to apply pressure to change the thickness of the body part, and estimates the concentration of a blood component from a second differential absorption spectrum obtained at the body part based on a statistical model of the blood component, the statistical model being established using a first differential absorption spectrum between the first and second absorption spectrums measured by the detection unit at different thicknesses of the body part and an actually measured concentration of the blood component.

In one embodiment of the apparatus, the signal processor generates signals for increasingly varying the thickness of the body part from an initial thickness to a first thickness and then a second thickness in correspondence with the actually measured concentration, obtains one of K first differential absorption spectrums between the first and second absorption spectrums measured from the body part at the first and second thicknesses, respectively, and performs multivariate statistical analysis on the K first differential absorption spectrums and K actually measured concentrations, thereby establishing the statistical model of the blood component. Further, the signal processor generates signals for increasingly varying the thickness of the body part from the initial thickness to the first thickness and then the second thickness, obtains the second differential absorption spectrum between the third absorption spectrum and the fourth absorption spectrum measured from the body part at the first and second thicknesses, respectively, and estimates the concentration of the blood component based on the statistical model. Preferably, a variation between the initial thickness and the first thickness is less than about 0.2 mm and a variation between the first thickness and the second thickness ranges from about 0.1 to 0.3 mm.

In another embodiment of the apparatus, the signal processor generates signals for increasingly varying the thickness of the body part from an initial thickness to a first thickness in correspondence with the actually measured concentration, holds the state in standby for a predetermined period of time, increasingly varies the thickness of the body part from the first thickness to a second thickness and then a third thickness, obtains one of K first differential absorption spectrums between the first and second absorption spectrums measured from the body part at the second and third thicknesses, respectively, and performs multivariate statistical analysis on the K first differential absorption spectrums and K actually measured concentrations, thereby establishing the statistical model of the blood component. Further, the signal processor generates signals for increasingly varying the thickness of the body part from the first thickness to the second thickness and then the third thickness, obtains the second differential absorption spectrum between the third absorption spectrum and the fourth absorption spectrum measured from the body part at the second and third thicknesses, respectively, and estimates the concentration of the blood component based on the statistical model. Preferably, a variation between the first thickness and the second thickness ranges from about 0.05 to 0.2 mm and a variation between the second thickness and the third thickness ranges from about 0.1 to 0.3 mm.

In the apparatus, the body-machine interface unit may include a beam guide portion transmitting light from the spectroscope, a light receiver collecting light from the body part, a holder attached to the light receiver, and a securing/compressing member that secures the body part between the beam guide portion and the light receiver and varies the thickness of the body part by adjusting the pressure applied to the body part.

BRIEF DESCRIPTION OF THE DRAWINGS

The above and other features and advantages of the present invention will become more apparent to those of ordinary skill in the art by describing in detail preferred embodiments thereof with reference to the attached drawings in which:

FIG. 5 is a detailed flowchart of operations 311 and 411, as shown in FIGS. 3 and 4, respectively;

DETAILED DESCRIPTION OF THE INVENTION

Figure 1:
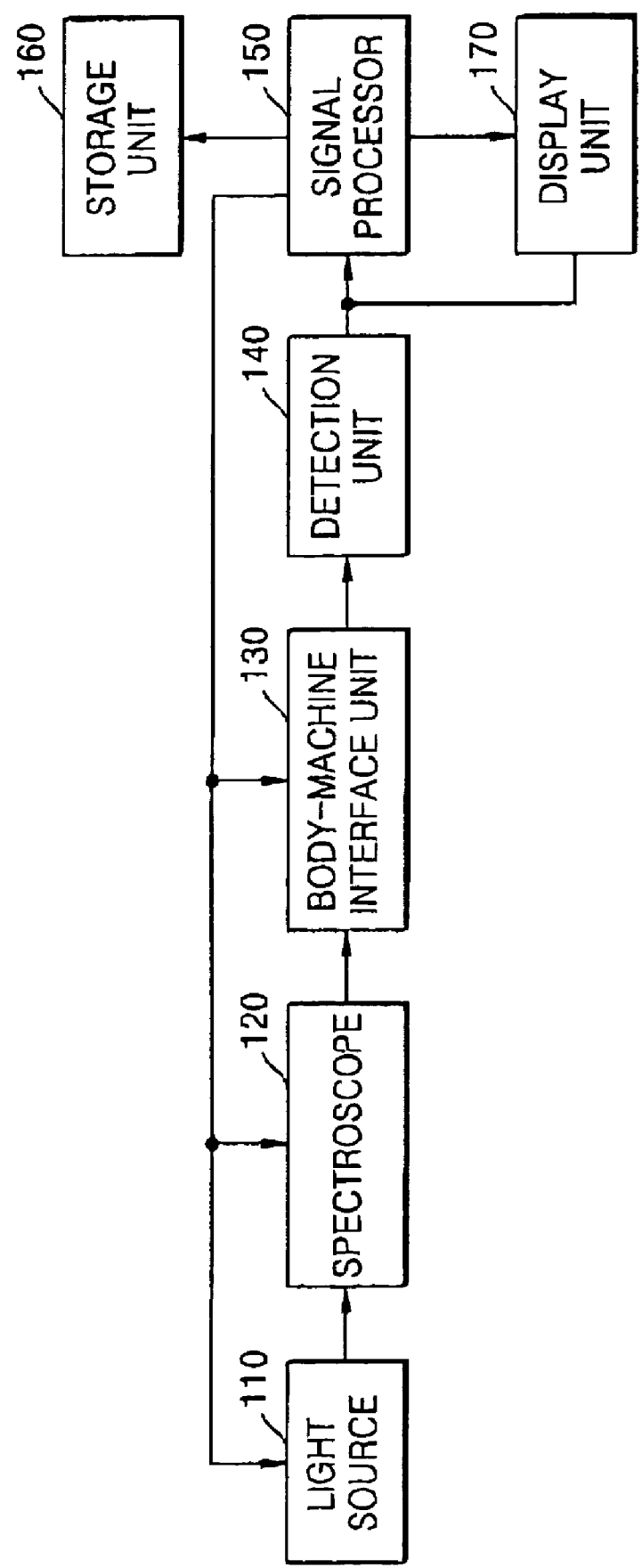
FIG. 1 is a block diagram of an apparatus for noninvasively measuring a concentration of a blood component according to an embodiment of the present invention.

Korean Patent Application No. 2003-17137, filed on Mar. 19, 2003, and entitled: "Method and Apparatus for Noninvasively Measuring a Blood Component," is incorporated by reference herein in its entirety.

The present invention will now be described more fully hereinafter with reference to the accompanying drawings, in which preferred embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

Seventy-three percent (73%) of a human body is composed of water, of which $1/3$ is extracellular water and $2/3$ is intracellular water. Three-quarters ($3/4$) of the extracellular water is an interstitial fluid and $1/4$ is an intravascular fluid. A blood glucose concentration of a human body indicates a concentration of glucose in blood, but a concentration of blood glucose in a capillary vessel is almost the same as a concentration of glucose in the interstitial fluid. The present invention is based on this feature of the blood glucose included in the interstitial fluid and the intravascular fluid.

FIG. 1 is a block diagram of an apparatus for noninvasively measuring a concentration of a blood component according to an embodiment of the present invention. The apparatus includes a light source 110, a spectroscope 120, a body-machine interface unit 130, a detection unit 140, a signal processor 150, a storage unit 160, and a display unit 170. The body-machine interface unit 130, the detection unit 140, the signal processor 150, the storage unit 160, and the display unit 170 or some of these components may be embodied in an integrated form.

Referring to FIG. 1, the light source 110 is implemented by, for example, a halogen lamp, and emits light having a predetermined wavelength band. The spectroscope 120 separates the light emitted from the light source 110. The body-machine interface unit 130 radiates the separated light onto a particular part of a subject, i.e., a human body, collects light transmitted through the human body, and provides the collected light to the detection unit 140. The body-machine interface unit 130 is mounted on a particular body part to be measured and is designed to vary a thickness of the particular body part according to a pressure applied to the particular body part and secure the particular body part.

The detection unit 140 detects a first through a fourth absorption spectrum from the light collected from the secured particular body part and radiated by the body-machine interface unit 130. The detection unit 140 provides the first and second absorption spectrums and the third and fourth absorption spectrums to the signal processor 150. The signal processor 150 is provided with a program for executing a method of noninvasively measuring a concentration of a blood component according to an embodiment of the present invention and includes a statistical model, which is established by the program to calculate the concentration of a particular blood component. The signal processor 150 measures absorption spectrums detected by the detection unit 140 from the soft tissue of the particular body part having different thicknesses, generates a first and a second differential absorption spectrum corresponding to a variation in thicknesses, and estimates a concentration of a particular blood component, which corresponds to the first differential absorption spectrum, using the statistical model.

The storage unit 160 stores the result of the processing performed by the signal processor 150. The display unit 170 displays the estimated concentration to inform a tester and/or a testee of the result of the measurement.

Figure 2A:
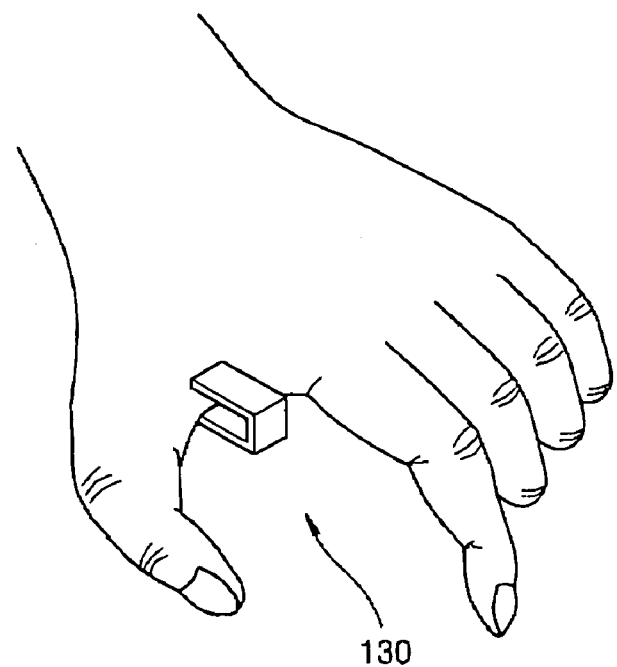
FIGS. 2A through 2C illustrate a shape and a detailed structure of a body-machine interface unit of FIG. 1.
Figure 2B:
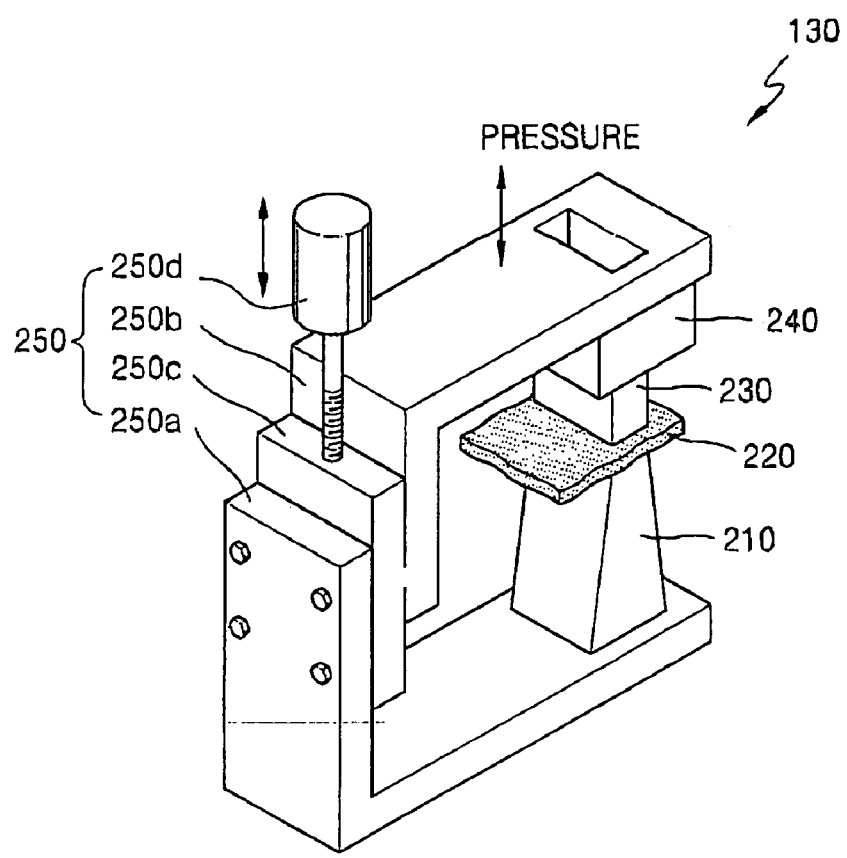
Figure 2C:
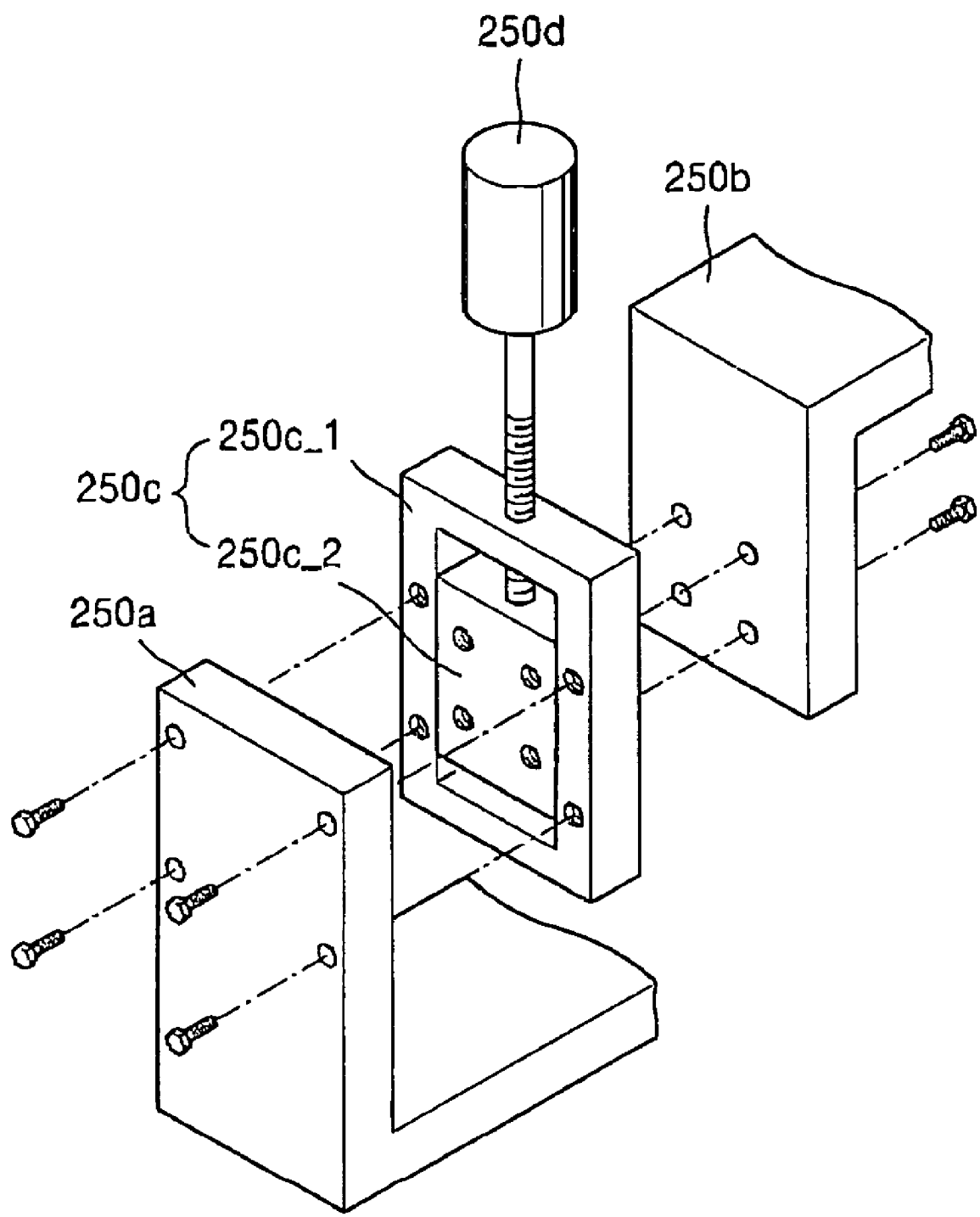

FIGS. 2A through 2C illustrate a shape and a detailed structure of the body-machine interface unit 130 of FIG. 1. The body-machine interface unit 130 has a clamp structure operable to compress a soft tissue. Preferably, the body-machine interface unit 130 has a shape that includes a pair of opposite, facing surfaces, as shown in FIG. 2A. As shown in FIG. 2B, the body-machine interface unit 130 includes a securing/compressing member 250, which secures an area of soft tissue and varies a thickness of the soft tissue.

Referring to FIG. 2B, the body-machine interface unit 130 includes a beam guide portion 210 transmitting light from the spectroscope 120, a light receiver 230 collecting light from a body part 220, a holder 240 attached to the light receiver 230, and the securing/compressing member 250. The securing/compressing member 250 secures the body part 220 between the beam guide portion 210 and the light receiver 230 and varies a thickness of the body part 220 by adjusting a pressure applied to the body part 220.

Referring to FIGS. 2B and 2C, the securing/compressing member 250 includes a first member 250$a$ installed parallel to the beam guide portion 210, a second member 250$b$ connected to the light receiver 230 through the holder 240, a fixing plate 250$c$_1 of a third member 250$c$ screw-coupled to the first member 250$a$, and a moving plate 250$c$_2 of the third member 250$c$ coupled to a screw-type handle 250$d$ and screw-coupled to the second member 250$b$. By manipulating the screw-type handle 250$d$, the second member 250$b$ coupled to the moving plate 250$c$_2 moves up and down, thereby adjusting the pressure applied to the body part 220 and adjusting the thickness of the body part 220. This principle is the same as that of common linear motors or lead-screw motors.

Figure 3:
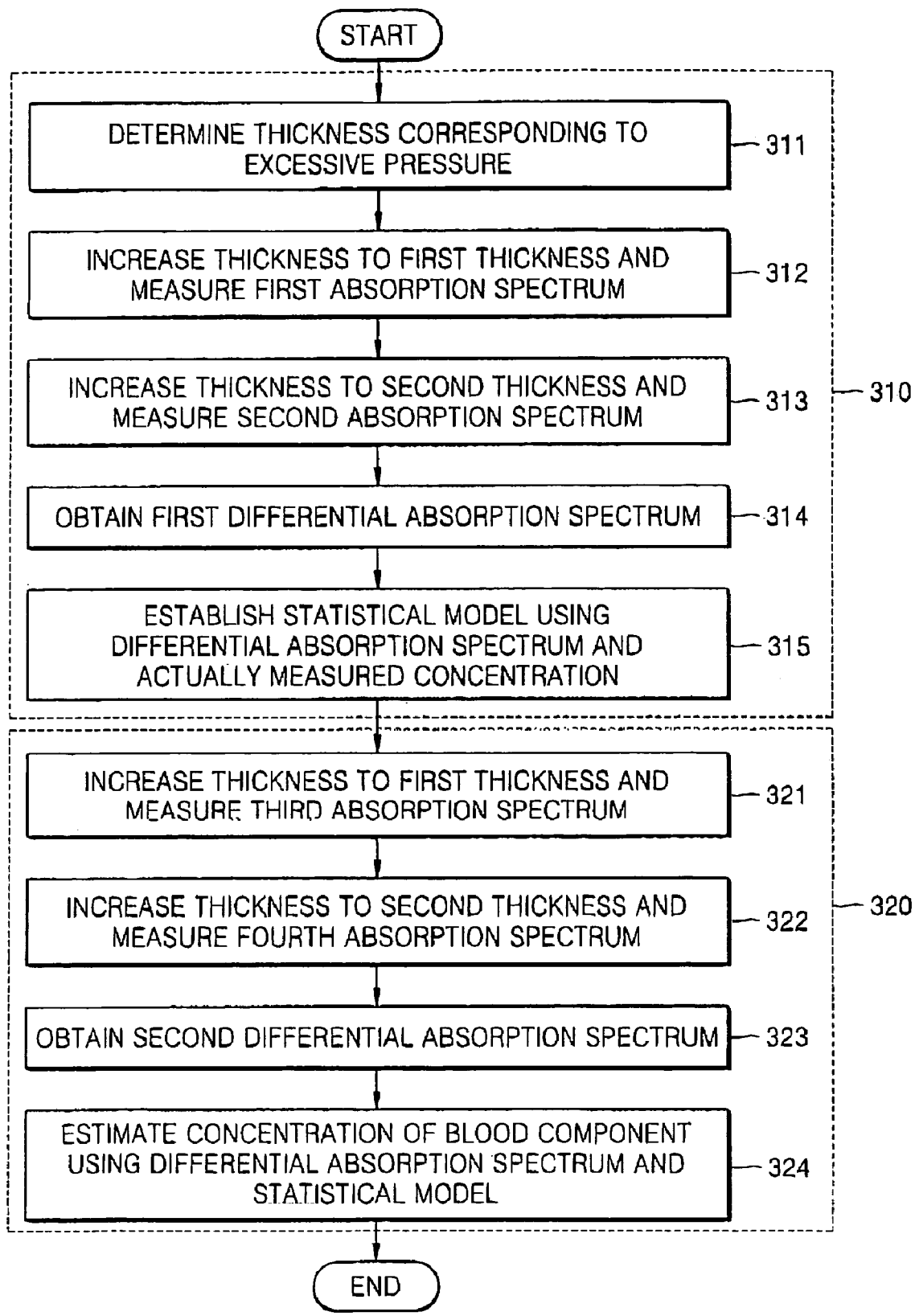
FIG. 3 is a flowchart of a method of noninvasively measuring a concentration of a blood component according to a first embodiment of the present invention.

FIG. 3 is a flowchart of a method of noninvasively measuring a concentration of a blood component according to a first embodiment of the present invention. The method includes an initial operation 310 for establishing a statistical model and a subsequent operation 320 for measuring a concentration of a blood component.

Referring to FIG. 3, operation 310 includes, in operation 311, determining an initial thickness corresponding to a predetermined excessive pressure applied to a subject's body part from which a concentration of a blood component is to be measured. The excessive pressure is a maximum pressure applied to the body part to determine an initial thickness of the body part. The initial thickness may vary depending on an individual person and a particular body part being compressed. Operation 311 will be described in greater detail with reference to FIG. 5.

In operation 312, the thickness of the body part is increased by a predetermined value from the initial thickness by controlling the body-machine interface unit 130. The increased thickness is set as a first thickness. Light having a particular wavelength band especially responding to a particular blood component is then radiated onto the body part, and a first absorption spectrum is measured from light transmitted through the body part. The body part may be a web of a hand between a thumb and an index finger, as shown in FIG. 2A, an earflap, an earlobe, a nose, or a lip, all of which have soft tissue. The wavelength band of light radiated onto the body part varies depending on a blood component to be measured. It is preferable that the wavelength band is about 1100 through 2500 nm when a blood component to be measured is glucose. It is preferable that a variation between the initial thickness and the first thickness does not exceed about 0.2 mm.

In operation 313, the thickness of the body part is again increased and set as a second thickness. Light having the particular wavelength band is then radiated onto the body part, and a second absorption spectrum is measured from light transmitted through the body part. It is preferable that a variation between the first thickness and the second thickness is about 0.1 through 0.3 mm.

In operation 314, a first differential absorption spectrum between the first absorption spectrum and the second absorption spectrum is obtained. The first differential absorption spectrum does not include a spectrum of an element, such as water or fat of the tissue, which disturbs or interferes with measurement of the concentration of the blood component. More specifically, the first and second absorption spectrums include errors caused by factors that are not related to the particular blood component to be measured. For example, factors such as the subject's body temperature, or a presence of hydrates, bones, cartilages, and collagen influence an optical measurement of vital components, but they are not directly related to the vital components. Thus, these errors can be removed by performing a subtraction between the first and second absorption spectrums.

Figure 8:
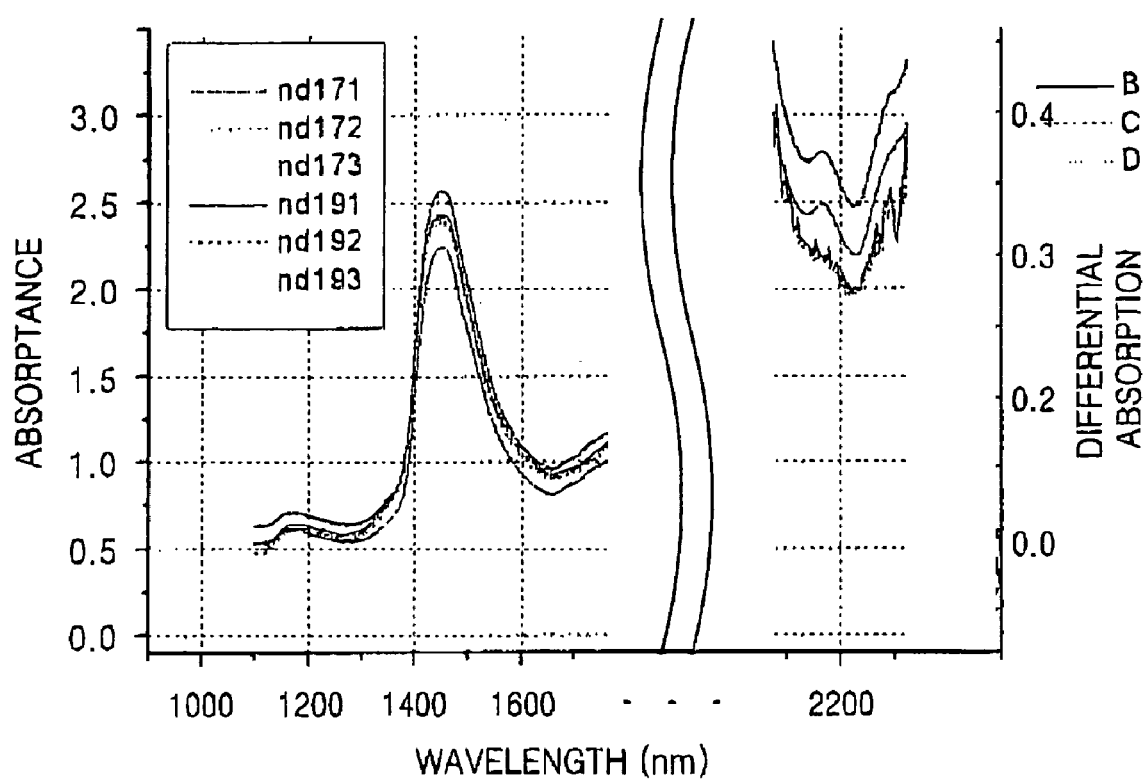
FIG. 8 is a graph showing examples of an absorption spectrum and a differential absorption spectrum when a thickness of a web of a hand is adjusted to about 1.7 mm and 1.9 mm.

FIG. 8 is a graph showing examples of the first and second absorption spectrums and the first differential absorption spectrum when the first and second thicknesses of a body part are set to about 1.7 (represented by line nd171) and 1.9 mm (represented by line nd193) at different portions of a web of a hand. It is preferable that the first differential absorption spectrum is processed using mean centering (MC), multiple scattering correction (MSC), or partial smoothing (PS). When PS is used, smoothing is performed only on a particular wavelength range, for example, a wavelength range having a high absorptance, among all of the data of the first differential absorption spectrum, and all of the original data except the particular wavelength range is used without modification.

Referring back to FIG. 3, in operation 315, a statistical model is established by performing multivariate statistical analysis on K concentrations of the particular blood component, which are actually measured from blood directly collected from the subject, and K first differential absorption spectrums obtained by repeating operations 312 through 314. This operation will be described in detail below.

The K first differential absorption spectrums can be expressed as Formula (1).

$$A_i = (A_{\lambda i1}, A_{\lambda i2}, \ldots, A_{\lambda in}), i=1, \ldots, K \qquad (1)$$

Here, a single first differential absorption spectrum $A_i$ can be expressed as a matrix of absorptances $A_{\lambda in}$ at n wavelengths $\lambda_{in}$ in the measurement wavelength band.

Next, a statistical model for calculating a concentration C of the particular blood component of the subject is established by Formula (2) using multivariate statistical analysis, for example, principal component regression or partial least square regression, of the K first differential absorption spectrums and the K actually measured concentrations.

$$C = \beta_1 A_{\lambda i1} + \beta_2 A_{\lambda i2} + \ldots + \beta_n A_{80\ in} \qquad (2)$$

More specifically, coefficients $\beta_1$ through $\beta_n$ of the absorptances $A_{\lambda in}$ at different wavelengths are obtained through the multivariate statistical analysis using Formula (2). The statistical model of the subject is stored in the signal processor 150.

When the concentration of the blood component is measured in operation 320, in operation 321, a third absorption spectrum is measured from the body part set to the first thickness, in operation 322, a fourth absorption spectrum is measured from the body part set to the second thickness, and, in operation 323, a second differential absorption spectrum between the third and fourth absorption spectrums is obtained. Operations 321 through 323 are performed in a manner substantially similar to operations 312 through 314.

In operation 324, a concentration of the particular blood component is estimated using the second differential absorption spectrum obtained in operation 323 and the statistical model established in operation 315. More specifically, the concentration C can be obtained by applying the values of $A_{\lambda i1}$ through $A_{\lambda in}$ obtained from the second differential absorption spectrum to Formula (2).

The first and second thicknesses are obtained when pressures lower than the excessive pressure are applied.

Figure 4A:
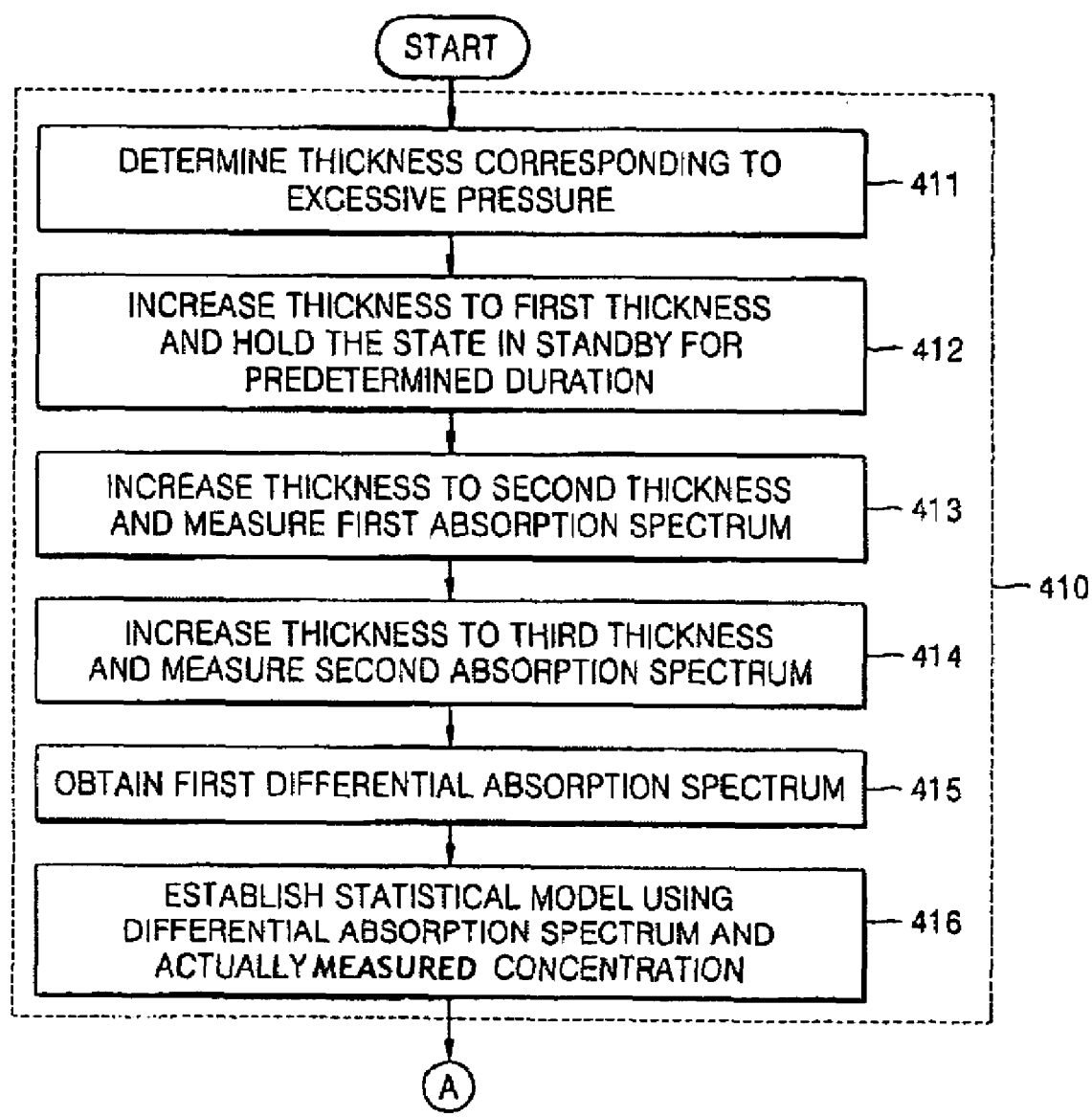
FIGS. 4A and 4B, collectively, are a flowchart of a method of noninvasively measuring a concentration of a blood component according to a second embodiment of the present invention.
Figure 4B:
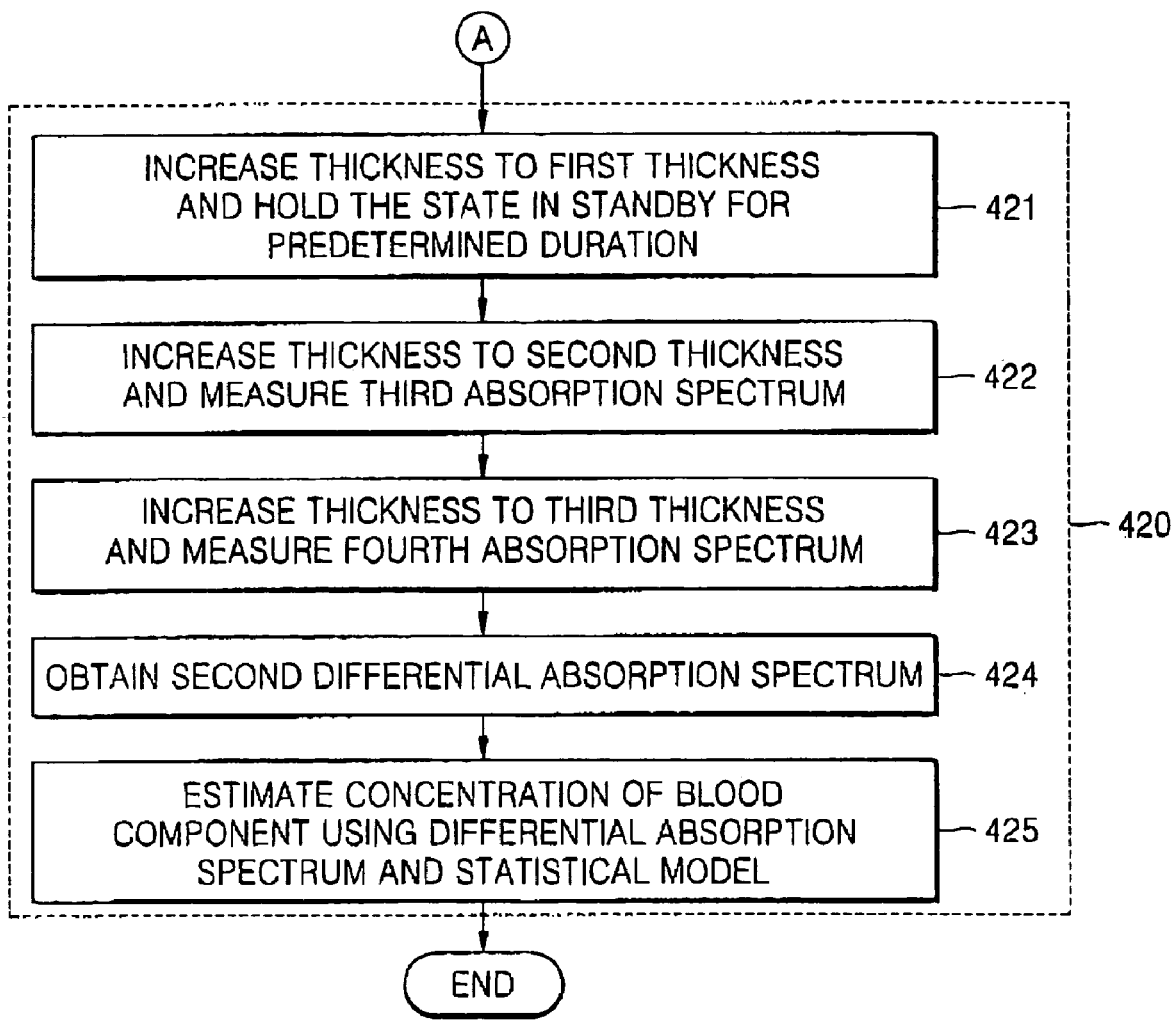

FIGS. 4A and 4B, collectively, are a flowchart of a method of noninvasively measuring a concentration of a blood component according to a second embodiment of the present invention. The method includes an initial operation 410 for establishing a statistical model and a subsequent operation 420 for measuring a concentration of a blood component.

Referring to FIG. 4A, operation 410 includes, in operation 411, determining an initial thickness corresponding to a predetermined excessive pressure applied to a subject's body part.

In operation 412, the thickness of the body part is increased by a predetermined value from the initial thickness by controlling the body-machine interface unit 130. The increased thickness is set as a first thickness, and this state is held in standby for a predetermined period of time. It is preferable that a variation of thicknesses is about 0.2 mm and the standby duration for stabilization is about 30 through 180 seconds.

In operation 413, the first thickness of the body part is increased to a second thickness. Light having a particular wavelength band is then radiated onto the body part, and a first absorption spectrum is measured. It is preferable that a variation of the first and second thicknesses is about 0.05 through 0.2 mm.

In operation 414, the second thickness of the body part is increased to a third thickness. Light having the particular wavelength band is then radiated onto the body part, and a second absorption spectrum is measured. It is preferable that a variation of the second and third thicknesses is about 0.1 through 0.3 mm.

In operation 415, a first differential absorption spectrum between the first absorption spectrum and the second absorption spectrum is obtained.

In operation 416, in the same manner as in the first embodiment, a statistical model is established by performing multivariate statistical analysis on K concentrations of the particular blood component, which are actually measured from blood directly collected from the subject, and K first differential absorption spectrums obtained by repeating operations 412 through 415.

Referring to FIG. 4B, operation 420 includes, in operation 421, setting the thickness of the body part to the first thickness and holding the state in standby for a predetermined duration, in operation 422, increasing the thickness of the body part to the second thickness and obtaining a third absorption spectrum from the body part set to the second thickness, in operation 423, increasing the thickness of the body part to the third thickness and obtaining a fourth absorption spectrum from the body part set to the third thickness, and, in operation 424, obtaining a second differential absorption spectrum between the third and fourth absorption spectrums.

In operation 425, a concentration of the particular blood component is obtained using the second differential absorption spectrum obtained in operation 424 and the statistical model established in operation 416. More specifically, the concentration C can be obtained by applying the values of $A_{\lambda i1}$ through $A_{80\ in}$ obtained from the second absorption spectrum to Formula (2).

The first through third thicknesses are thicknesses that are obtained when pressures lower than the excessive pressure are applied.

When a wavelength range of a light source is changed in the methods shown in FIGS. 3 and 4, components other than glucose, such as hemoglobin, cholesterol, and medicines, may be measured.

FIG. 5 is a detailed flowchart of operations 311 and 411 shown in FIGS. 3 and 4, respectively. For clarity of the description, it is assumed that a body part having soft tissue is a web of the hand.

Referring to FIG. 5, in operation 511, under the control of the body-machine interface unit 130, the thickness of the web is changed by a predetermined value, for example, about 0.1 mm, from a first thickness, for example, about 1.5 mm, to a second thickness, for example, about 2.2 mm. Since the body part is elastic, a reaction force thereof rapidly changes over time in an initial compressing stage. However, as the compressing continues, the elasticity of the body part becomes almost nonexistent, and thereafter, the reaction force barely changes. Accordingly, it is preferable that a pressure is applied onto the body part for about 120 seconds. The thickness of the body part sensed by the pressure sensor 240 at this time is provided to the signal processor 150.

In operation 512, variations of reaction forces of the web of the hand are measured at different thicknesses of the web, which are adjusted by increasing or decreasing a pressure applied to the web for about 120 seconds. When the thickness of the web is changed from about 1.5 mm (represented by lines th151, th152 and th153) to about 2.2 mm (represented by lines th221, th222 and th223), variations of reaction forces are shown in a graph of FIG. 6.

Figure 6:
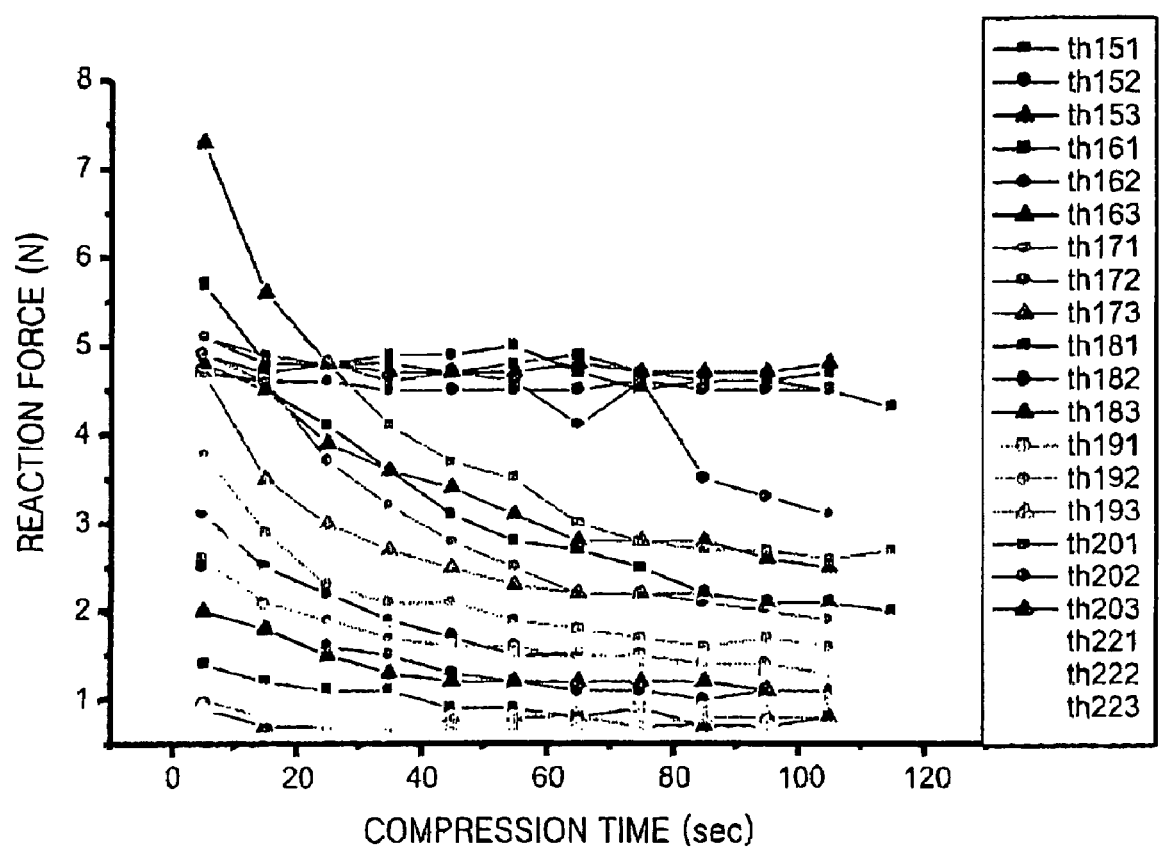
FIG. 6 is a graph showing variations of reaction forces at different thicknesses of a web of a hand over time.

In operation 513, a thickness corresponding to the excessive pressure is determined based on the graph shown in FIG. 6. Referring to FIG. 6, when the thickness of the web is about 1.5 through 1.6 mm, that is, when a pressure exceeds the excessive pressure, the web has constant reaction force even as time lapses. However, when the thickness of the web increases above about 1.6 mm, that is, when an applied pressure decreases, the reaction force of the web decreases or becomes almost zero as time lapses. A pressure or a reaction force of a human body at a boundary thickness between a thickness maintaining the reaction force constant and a thickness decreasing the reaction force, about 1.6 mm in FIG. 6, is determined as the excessive pressure, and the thickness at the excessive pressure is determined as the initial thickness.

Figure 7:
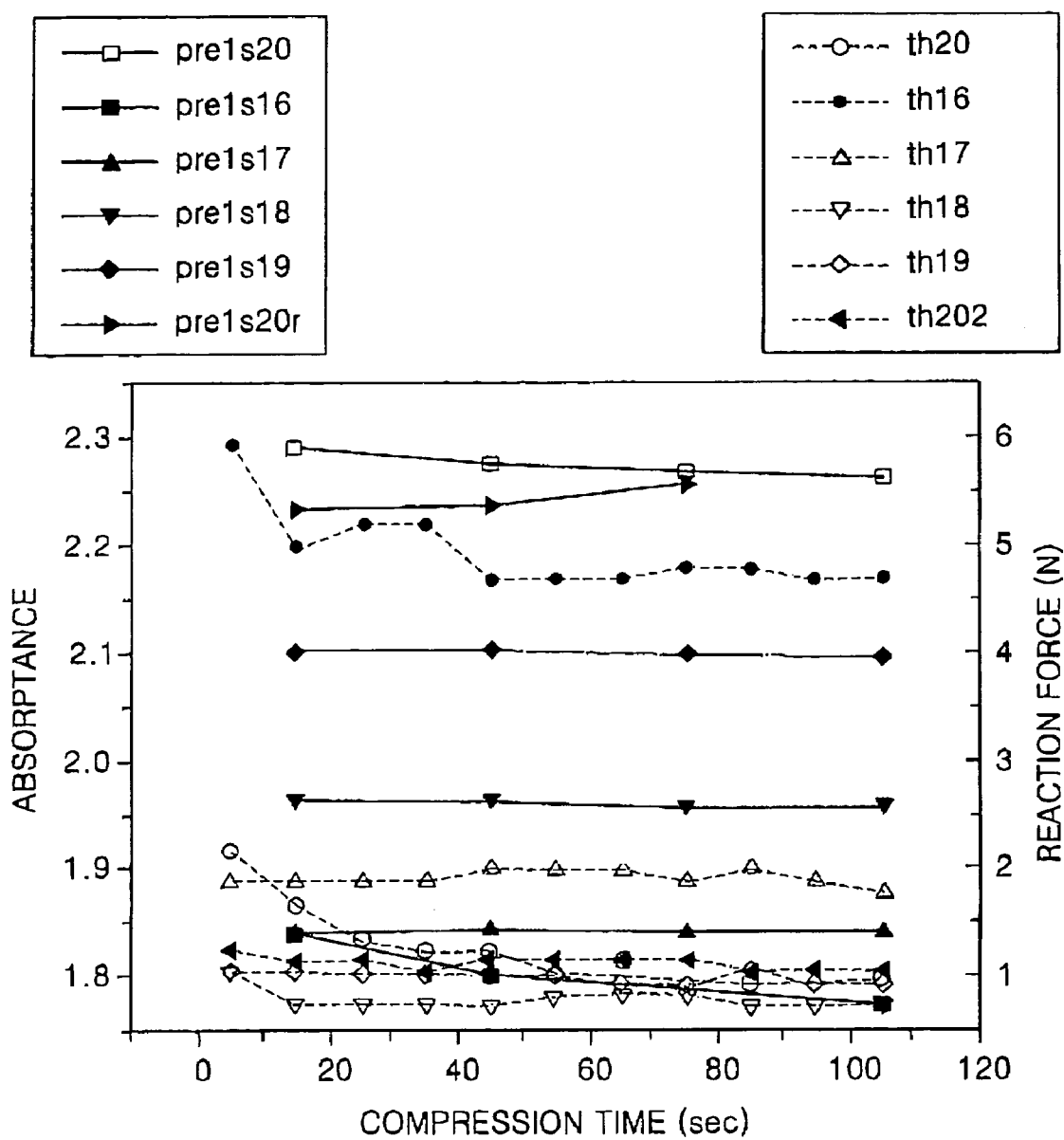
FIG. 7 is a graph showing changes in reaction force and absorptance of a web versus changes in thickness of the web of a hand.

FIG. 7 is a graph showing changes in reaction force and absorptance of the web versus changes in thickness of the web. The changes in reaction force were compared when the initial thickness of the web was set to 2.0 mm (represented by line th20), was then decreased to 1.6 mm (represented by line th16), and was then changed to 1.7 mm, 1.8 mm, 1.9 mm, and 2.0 mm (represented by lines th17, th18, th19, and th202, respectively). The changes in absorptance were compared when the initial thickness of the web was set to 2.0 mm (represented by line pre 1s20), was then decreased to 1.6 mm (represented by line pre 1s16), and was then changed to 1.7 mm, 1.8 mm, 1.9 mm, and 2.0 mm (represented by lines pre1s17, pre1s18, pre1s19, and pre1s20r, respectively).

Here, each thickness was maintained for 120 seconds, before being changed. Referring to FIG. 7, when the thickness was changed to 1.7 mm, 1.8 mm, 1.9 mm, and 2.0 mm above a thickness of 1.6 mm corresponding to the excessive pressure, the absorptance almost linearly changed while the reaction force was very slowly restored. More specifically, it can be inferred that a body part having soft tissue is released from pressure, an extracellular fluid moves very swiftly, but the compressed tissue is slowly restored. Based on such a difference between the two conditions, only a spectrum of the extracellular fluid can be separated. Accordingly, it is preferable that a thickness is changed within a range that can induce only such changes in the fluid. These preferable changes in thickness can be achieved by applying lower pressures than the excessive pressure.

Figure 9A:
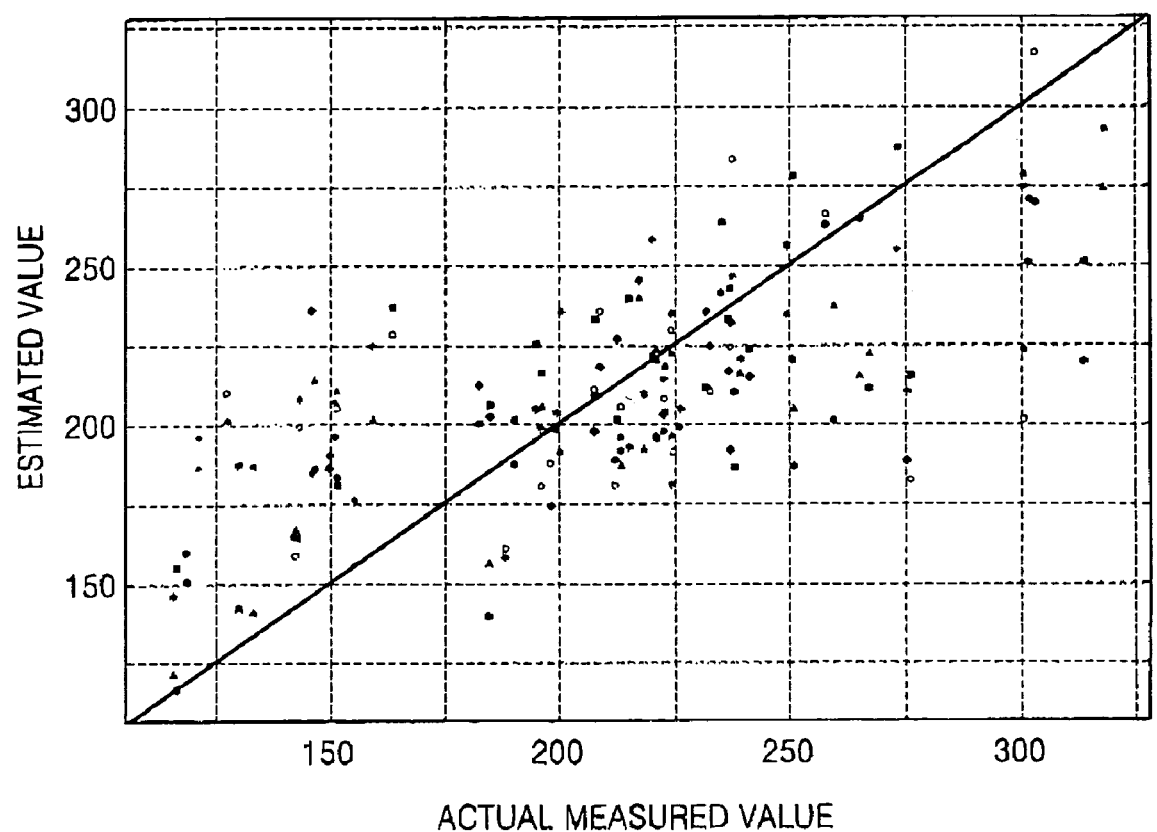
FIGS. 9A and 9B are graphs showing distributions of estimates of glucose values with respect to a reference value when calibration and cross-validation are performed when the first and second thicknesses are about 1.5 mm and 1.7 mm.
Figure 9B:
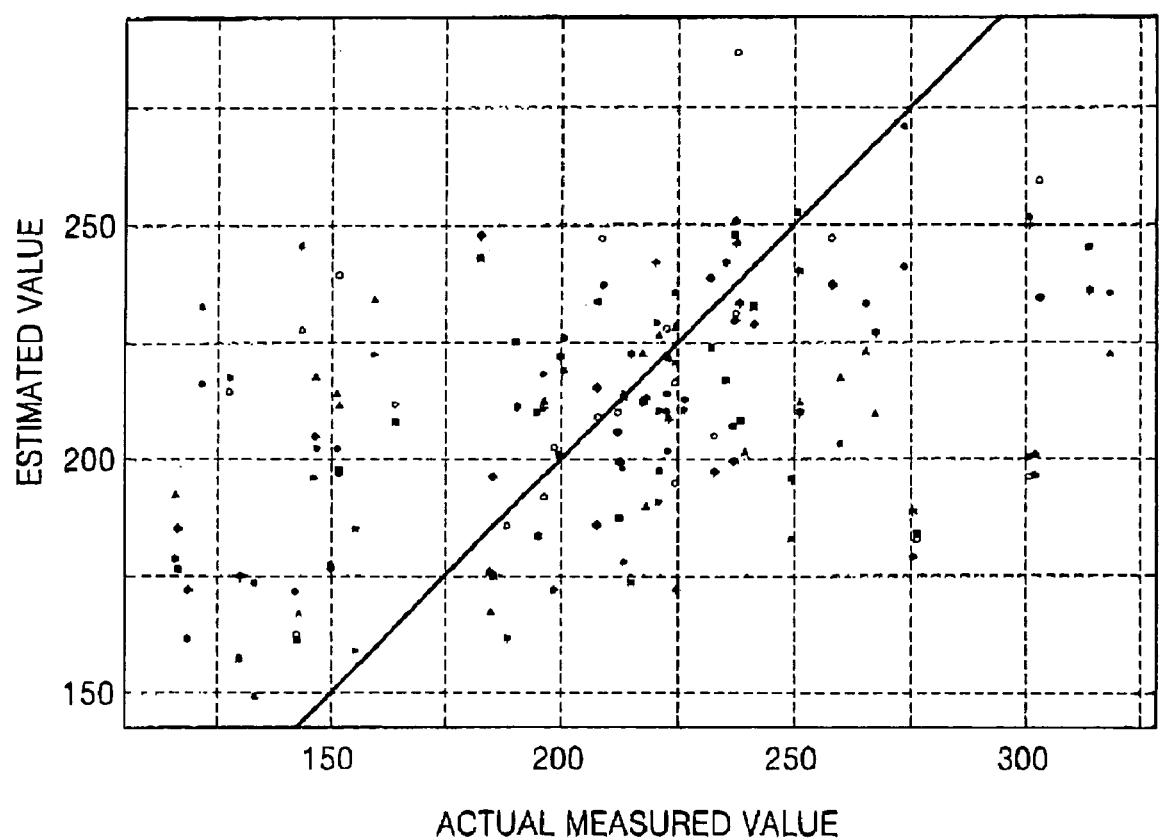

FIGS. 9A and 9B are graphs showing distributions of estimates of glucose values with respect to a reference value when calibration and cross-validation were performed when the first and second thicknesses were about 1.5 mm and 1.7 mm. A thickness of about 1.5 mm was obtained when a pressure greater than the excessive pressure was applied to the web. It may be seen that when glucose is measured using a statistical model established when the first and second thicknesses are about 1.5 mm and 1.7 mm, an error in the statistical model is great and linearity is poor. More specifically, as a result of calibration, standard error of calibration (SEC)=38.83 mg/dl (ten factors) and R=0.672. As a result of cross-validation, standard error of cross-validation (SECV)= 45.764 mg/dl (three factors) and R=0.429.

Figure 10A:
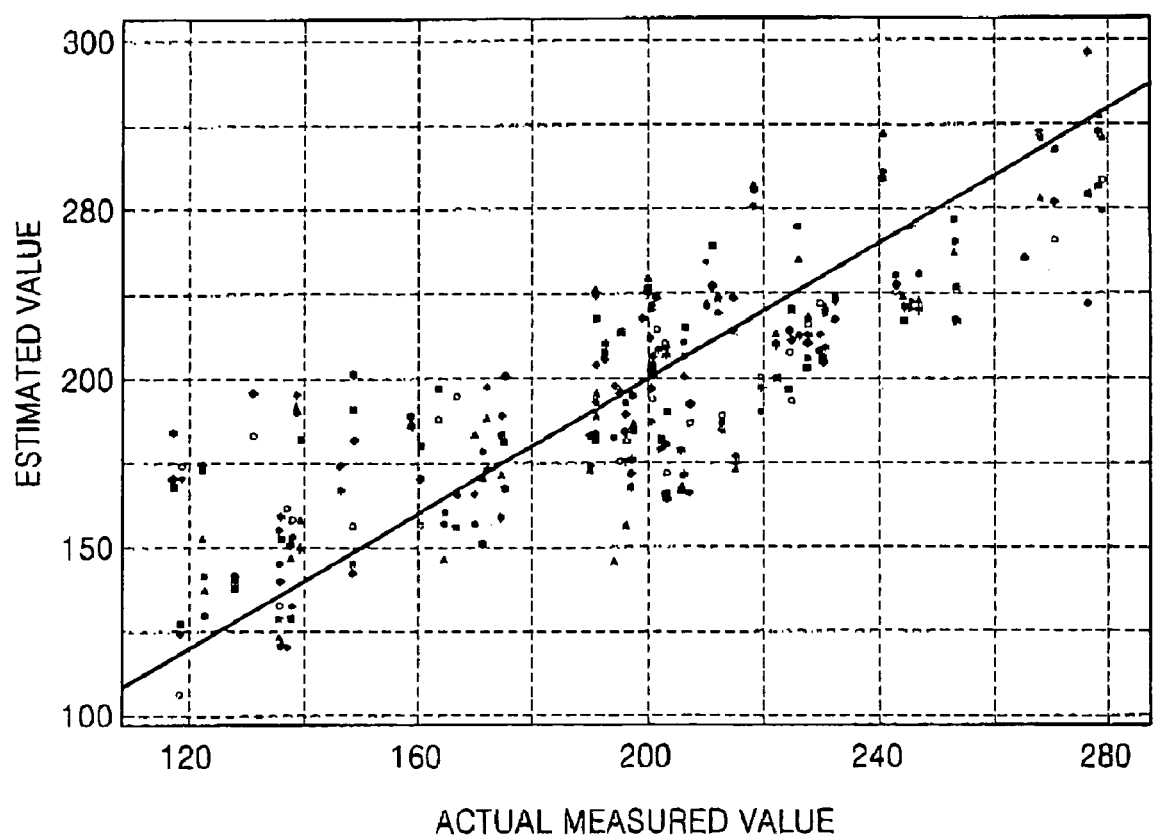
FIGS. 10A and 10B are graphs showing distributions of estimates of glucose values with respect to a reference value when calibration and cross-validation are performed when the first and second thicknesses are about 1.7 mm and 1.9 mm.
Figure 10B:
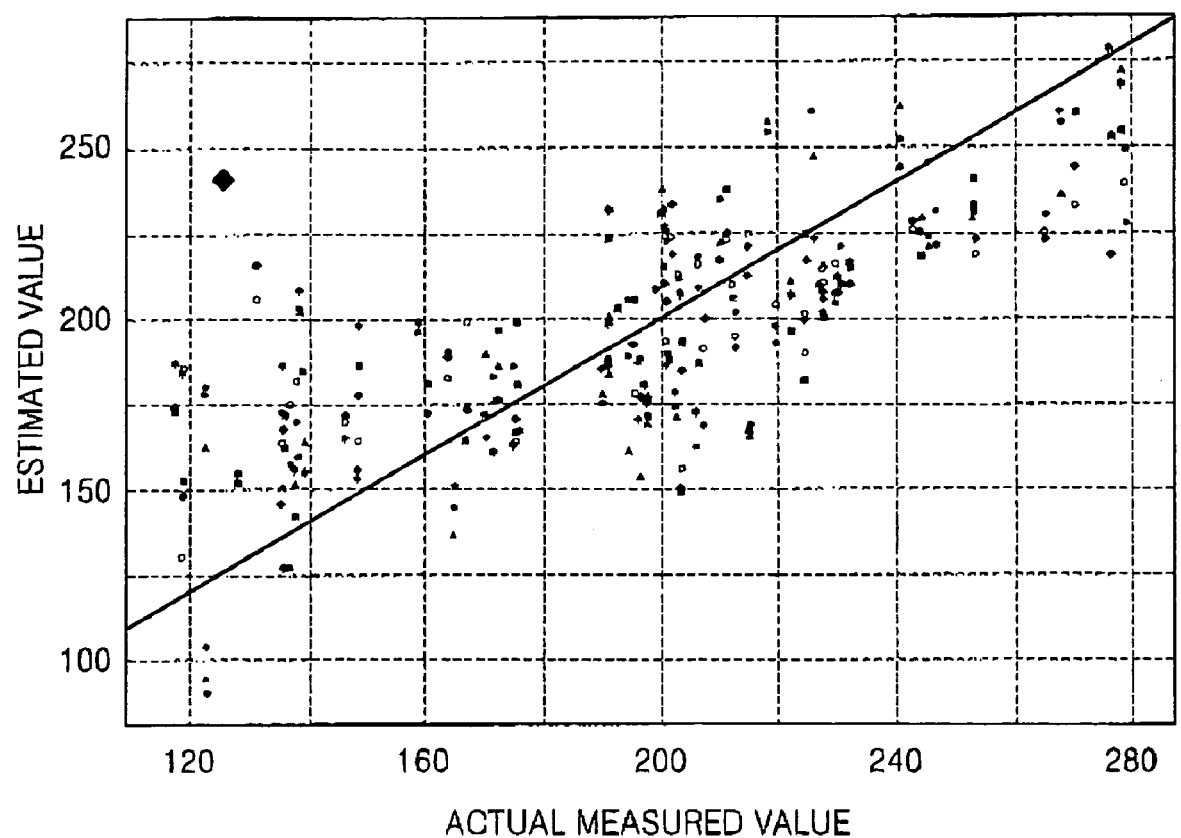

FIGS. 10A and 10B are graphs showing distributions of estimations of glucose values with respect to a reference value when calibration and cross-validation were performed when the first and second thicknesses were about 1.7 mm and 1.9 mm. Thicknesses of about 1.7 mm and 1.9 mm were obtained when pressures lower than the excessive pressure were applied to the web. It may be seen that when glucose is measured using a statistical model established when the first and second thicknesses are about 1.7 mm and 1.9 mm, an error in the statistical model is small and linearity is improved. More specifically, as a result of calibration, SEC=23.876 mg/dl (ten factors) and R=0.826. As a result of cross-validation, SECV=27.957 mg/dl (seven factors) and R=0.739. Thus, the standard error is decreased significantly.

The present invention can be realized as a code that is recorded on a computer readable recording medium and can be read by a computer. The computer readable recording medium may be any type of medium on which data that can be read by a computer system can be recorded, for example, a ROM, a RAM, a CD-ROM, a magnetic tape, a floppy disc, or an optical data storage device. The present invention can also be realized as carrier waves (for example, transmitted through Internet). Alternatively, computer readable recording media may be distributed among computer systems connected through a network so that the present invention may be realized as a code that is stored in the recording media and can be read and executed in the computers. Functional programs, codes, and code segments for implementing the present invention can be easily inferred by programmers in the art of the present invention.

As described above, in the present invention, a statistical model is established using a first differential absorption spectrum corresponding to a variation of the amounts of extracellular fluid at different thicknesses of a body part having soft tissue, which are adjusted by applying lower pressures than an excessive pressure to the body part, and a concentration of a particular blood component can be estimated using a second differential absorption spectrum and the statistical model. Accordingly, an influence of the extracellular fluid can be increased, and factors disturbing or interfering with the measurement of the concentration of the particular blood component can be removed. Therefore, the concentration of the particular blood component can be more accurately estimated.

In addition, since a thickness corresponding to an excessive pressure is determined for each person, and a statistical model is established on the basis of the thickness, measurement conditions for each person can be numerically expressed. Moreover, since only an effect of a fluid can be separated, a concentration can be accurately estimated. Since the fluid, rather than tissue, is moved by decreasing a pressure applied to soft tissue, reproducibility of the measurement of spectrum is satisfactory.

Preferred embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A method of noninvasively measuring a concentration of a blood component, comprising:
    (a) varying a thickness of a body part of a subject, measuring absorption spectrums at different thicknesses of the body part, obtaining a first differential absorption spectrum between the absorption spectrums measured at different thicknesses, actually measuring concentrations of the blood component, and establishing a multivariate statistical model using the first differential absorption spectrum and the actually measured concentrations; and
    (b) estimating the concentration of the blood component using a second differential absorption spectrum obtained with respect to the body part based on the multivariate statistical model.

2. The method as claimed in claim 1, wherein (a) comprises:
    (a1) determining an initial thickness of the body part of the subject;
    (a2) increasing the thickness of the body part from the initial thickness to a first thickness and measuring a first absorption spectrum with respect to the body part;
    (a3) increasing the thickness of the body part from the first thickness to a second thickness and measuring a second absorption spectrum with respect to the body part;
    (a4) generating one of K first differential absorption spectrums between the first and second absorption spectrums;
    (a5) obtaining the K first differential absorption spectrums by repeating operations (a2) through (a4) K times in correspondence with K concentrations of the blood component actually measured from the subject; and
    (a6) establishing the multivariate statistical model of the blood component by performing multivariate statistical analysis on the K first differential absorption spectrums and the K concentrations actually measured.

3. The method as claimed in claim 2, wherein (b) comprises:
    (b1) increasing the thickness of the body part from the initial thickness to the first thickness and measuring a third absorption spectrum with respect to the body part;

(b2) increasing the thickness of the body part from the first thickness to the second thickness and measuring a fourth absorption spectrum with respect to the body part;

(b3) generating the second differential absorption spectrum between the third and fourth absorption spectrums; and (b4) estimating the concentration of the blood component using the second differential absorption spectrum generated in operation (b3) and the multivariate statistical model.

4. The method as claimed in claim 3, wherein a variation between the initial thickness and the first thickness is less than about 0.2 mm.

5. The method as claimed in claim 3, wherein a variation between the first thickness and the second thickness ranges from about 0.1 to 0.3 mm.

6. The method as claimed in claim 1, wherein (a) comprises:

(a1) determining an initial thickness of the body part of the subject;

(a2) increasing the thickness of the body part from the initial thickness to a first thickness and holding the state in standby for a predetermined period of time;

(a3) increasing the thickness of the body part from the first thickness to a second thickness and measuring a first absorption spectrum with respect to the body part;

(a4) increasing the thickness of the body part from the second thickness to a third thickness and measuring a second absorption spectrum with respect to the body part;

(a5) generating one of K first differential absorption spectrums between the first and second absorption spectrums;

(a6) obtaining the K first differential absorption spectrums by repeating operations (a2) through (a5) K times in correspondence with K concentrations of the blood component actually measured from the subject; and (a7) establishing the multivariate statistical model of the blood component by performing multivariate statistical analysis on the K first differential absorption spectrums and the K concentrations actually measured.

7. The method as claimed in claim 6, wherein (b) comprises:

(b1) increasing the thickness of the body part from the initial thickness to the first thickness and holding the state in standby for the predetermined period of time;

(b2) increasing the thickness of the body part from the first thickness to the second thickness and measuring a third absorption spectrum with respect to the body part;

(b3) increasing the thickness of the body part from the second thickness to the third thickness and measuring a fourth absorption spectrum with respect to the body part;

(b4) generating the second differential absorption spectrum between the third and fourth absorption spectrums; and (b5) estimating the concentration of the blood component using the second differential absorption spectrum generated in operation (b4) and the multivariate statistical model.

8. The method as claimed in claim 7, wherein the predetermined period of time ranges from about 30 to 180 seconds.

9. The method as claimed in claim 7, wherein a variation between the first thickness and the second thickness ranges from about 0.05 to 0.2 mm.

10. The method as claimed in claim 7, wherein a variation between the second thickness and the third thickness ranges from about 0.1 to 0.3 mm.

11. A computer readable recording medium having recorded therein a program for executing the method as claimed in claim 1.

12. An apparatus for noninvasively measuring a concentration of a blood component, comprising:

a light source that emits light;

a spectroscope that separates the light emitted from the light source into components of different wavelengths;

a body-machine interface unit, which is adapted to be mounted on a body part of a subject, that radiates the light from the spectroscope onto the body part, collects light transmitted through the body part, varies a thickness of the body part according to a pressure applied to the body part, and secures the body part;

a detection unit that detects a first through a fourth absorption spectrum from the light collected by the body-machine interface unit; and a signal processor that generates a signal for the body-machine interface unit to apply pressure to change the thickness of the body part, and estimates the concentration of a blood component from a second differential absorption spectrum obtained at the body part based on a multivariate statistical model of the blood component, the multivariate statistical model being established using a first differential absorption spectrum between the first and second absorption spectrums measured by the detection unit at different thicknesses of the body part and an actually measured concentration of the blood component.

13. The apparatus as claimed in claim 12, wherein the signal processor generates signals for increasingly varying the thickness of the body part from an initial thickness to a first thickness and then a second thickness in correspondence with the actually measured concentration, obtains one of K first differential absorption spectrums between the first and second absorption spectrums measured from the body part at the first and second thicknesses, respectively, and performs multivariate statistical analysis on the K first differential absorption spectrums and K actually measured concentrations, thereby establishing the multivariate statistical model of the blood component.

14. The apparatus as claimed in claim 13, wherein the signal processor generates signals for increasingly varying the thickness of the body part from the initial thickness to the first thickness and then the second thickness, obtains the second differential absorption spectrum between the third absorption spectrum and the fourth absorption spectrum measured from the body part at the first and second thicknesses, respectively, and estimates the concentration of the blood component based on the multivariate statistical model.

15. The apparatus as claimed in claim 14, wherein a variation between the initial thickness and the first thickness is less than about 0.2 mm.

16. The apparatus as claimed in claim 14, wherein a variation between the first thickness and the second thickness ranges from about 0.1 to 0.3 mm.

17. The apparatus as claimed in claim 12, wherein the signal processor generates signals for increasingly varying the thickness of the body part from an initial thickness to a first thickness in correspondence with the actually measured concentration, holds the state in standby for a predetermined period of time, increasingly varies the thickness of the body part from the first thickness to a second thickness and then a third thickness, obtains one of K first differential absorption spectrums between the first and second absorption spectrums measured from the body part at the second and third thicknesses, respectively, and performs multivariate statistical analysis on the K first differential absorption spectrums and K actually measured concentrations, thereby establishing the multivariate statistical model of the blood component.

18. The apparatus as claimed in claim 17, wherein the signal processor generates signals for increasingly varying the thickness of the body part from the first thickness to the second thickness and then the third thickness, obtains the second differential absorption spectrum between the third absorption spectrum and the fourth absorption spectrum measured from the body part at the second and third thicknesses, respectively, and estimates the concentration of the blood component based on the multivariate statistical model.

19. The apparatus as claimed in claim 18, wherein a variation between the first thickness and the second thickness ranges from about 0.05 to 0.2 mm.

20. The apparatus as claimed in claim 19, wherein a variation between the second thickness and the third thickness ranges from about 0.1 to 0.3 mm.

21. The apparatus as claimed in claim 12, wherein the body-machine interface unit comprises:
 a beam guide portion transmitting light from the spectroscope;
 a light receiver collecting light from the body part;
 a holder attached to the light receiver; and
 a securing/compressing member that secures the body part between the beam guide portion and the light receiver and varies the thickness of the body part by adjusting the pressure applied to the body part.

* * * * *